(12) United States Patent
Frances

(10) Patent No.: US 8,262,391 B2
(45) Date of Patent: *Sep. 11, 2012

(54) DENTAL COMPOSITION BASED ON SILICONE CROSSLINKABLE BY CATION PROCESS

(75) Inventor: Jean-Marc Frances, Meyzieu (FR)

(73) Assignee: Bluestar Silicones France SAS, Lyons (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/370,817

(22) Filed: Mar. 8, 2006

(65) Prior Publication Data

US 2006/0178444 A1 Aug. 10, 2006

Related U.S. Application Data

(63) Continuation of application No. 09/806,648, filed on Jun. 2, 2003, now abandoned.

(30) Foreign Application Priority Data

Oct. 2, 1998 (FR) ...................................... 98 12374

(51) Int. Cl.
*A61K 6/093* (2006.01)
*A61C 5/00* (2006.01)
*A61F 2/00* (2006.01)

(52) U.S. Cl. ......... 433/228.1; 522/29; 522/66; 522/168; 522/170; 523/115; 523/116

(58) Field of Classification Search .................. 522/7, 8, 522/29, 66, 99, 148, 170, 172, 908, 83, 129, 522/168; 523/115, 116, 117, 109; 433/222.1, 228.1, 201.2, 202.1, 218

See application file for complete search history.

(56) References Cited

U.S. PATENT DOCUMENTS

| | | | |
|---|---|---|---|
| 5,260,349 A * | 11/1993 | Crivello | 522/31 |
| 5,385,954 A | 1/1995 | Palazzotto | 522/29 |
| 5,401,528 A | 3/1995 | Schmidt | 427/2.26 |
| 5,468,902 A * | 11/1995 | Castellanos et al. | 568/6 |
| 5,512,605 A * | 4/1996 | Eckberg et al. | 522/31 |
| 5,693,688 A | 12/1997 | Priou | 522/25 |
| 5,980,253 A * | 11/1999 | Oxman et al. | 433/228.1 |
| 6,084,004 A * | 7/2000 | Weinmann et al. | 522/25 |
| 6,245,828 B1 * | 6/2001 | Weinmann et al. | 522/148 |
| 6,417,243 B1 | 7/2002 | Peeters | 522/31 |
| 6,423,378 B1 | 7/2002 | Cotting | 427/387 |
| 6,652,281 B1 * | 11/2003 | Eckhardt et al. | 433/219 |
| 6,747,071 B1 | 6/2004 | Frances | 522/148 |
| 6,864,311 B2 * | 3/2005 | Breunig et al. | 524/588 |
| 2004/0171717 A1 | 9/2004 | Frances | 523/115 |
| 2007/0149136 A1 * | 6/2007 | Iwami | 455/67.14 |

FOREIGN PATENT DOCUMENTS

CA 2 232 960 9/1998

* cited by examiner

*Primary Examiner* — Susan W Berman
(74) *Attorney, Agent, or Firm* — SNR Denton US LLP

(57) ABSTRACT

The invention concerns dental compositions. Said composition comprises (1) a silicone crosslinkable and/or polymerizable by cationic process; (2) an efficient amount of at least an initiator such as an organometallic complex borate; and (3) a dental filler present in the composition in a proportion of at least 10 wt. % relative to the composition total weight. Said dental compositions are useful for making dental prostheses or for dental restoration.

9 Claims, No Drawings

DENTAL COMPOSITION BASED ON SILICONE CROSSLINKABLE BY CATION PROCESS

This application is a continuation of U.S. application Ser. No. 09/806,648, filed on Jun. 2, 2003 now abandoned.

The field of the invention is that of dental compositions. More precisely, the dental compositions used in the context of the present invention can be used for producing dental prostheses and for dental restoration.

Up until now, to produce dental compositions for the preparation of dental prostheses or of dental restoration materials, it is possible to use resins based on photopolymerizable acrylates. These ready-to-formulate products exhibit however upon use problems of irritation and potential problems of toxicity.

In addition, these products have the major disadvantage of causing high volume shrinkage during their polymerization, which makes their use complex and difficult for the production of dental prostheses or of dental restoration materials. Problems of attachment due to the volume shrinkage or to the lack of adherence of the polymers used are in particular observed.

The object of the present invention is to provide novel dental compositions which do not exhibit the disadvantages of the prior art. These novel dental compositions, which are polymerizable and/or crosslinkable in an oral environment, have markedly improved qualities, in particular as regards the very marked reduction in the phenomenon of shrinkage of the dental compositions used for the production of dental prostheses or of dental restoration materials.

The polymerizable and/or crosslinkable dental composition according to the invention comprises:

(1) at least one crosslinkable and/or polymerizable silicone oligomer or polymer which is liquid at room temperature or which is heat-meltable at a temperature of less than 100° C., and which comprises:
at least one unit of formula (I):

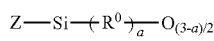

in which:
a=0, 1 or 2,
$R^0$, identical or different, represents an alkyl, cycloalkyl, aryl, vinyl, hydrogeno or alkoxy radical, preferably a $C_1$-$C_6$ lower alkyl,
Z, identical or different, is an organic substituent comprising at least one reactive epoxy, and/or alkenyl ether and/or oxetane and/or dioxolane and/or carbonate functional group, and preferably Z being an organic substituent comprising at least one reactive epoxy and/or dioxolane functional group, and at least two silicon atoms;

(2) an effective quantity of at least one organometallic complex borate-type photoinitiator having a residual light absorption of between 200 and 500 nm;

(3) and at least one dental filler present in a proportion of at least 10% by weight relative to the total weight of the composition.

According to a first variant of the present invention, the dental composition is polymerizable and/or crosslinkable under activation by the thermal route and/or by the photochemical route.

In general, the photochemical activation is carried out under UV radiation. More particularly, UV radiation having a wavelength of the order of 200 to 500 nm is used for the production of dental prostheses and UV-visible radiation having a wavelength greater than 400 nm for the production of restoration materials. A wavelength greater than 400 nm allows crosslinking and/or polymerization in an oral environment.

The silicone polymer or oligomer (1) has the advantage, compared with organic resins, of being transparent to UV-visible light and therefore its use makes it possible to obtain materials which are very thick and whose photocrosslinking occurs in a short time.

The reactive functional groups Z of the silicone polymer or oligomer (1) may be highly varied. However, particularly advantageous dental compositions are obtained when the silicone oligomer or polymer (1) comprises at least one (FS) unit in which Z represents an organic substituent Z1 comprising at least one reactive epoxy, and/or dioxolane functional group, and preferably at least one reactive epoxy functional group.

According to two advantageous alternatives of the present invention, the silicone oligomer or polymer (1) with at least one reactive epoxy and/or dioxolane functional group Z1, and preferably at least one reactive epoxy functional group may:
(i) either comprise only this (these) type(s) of reactive functional group(s) Z1,
(ii) or comprise other reactive functional groups Z such as the reactive alkenyl ether, oxetane and/or carbonate functional groups Z2.

In the case of the first alternative (i), the dental composition may also comprise other silicone oligomers and/or polymers comprising other reactive functional groups Z2 such as alkenyl ether, oxetane and/or carbonate functional groups and optionally reactive functional groups Z1.

By way of examples of reactive functional groups Z, these may in particular be chosen from the following radicals:

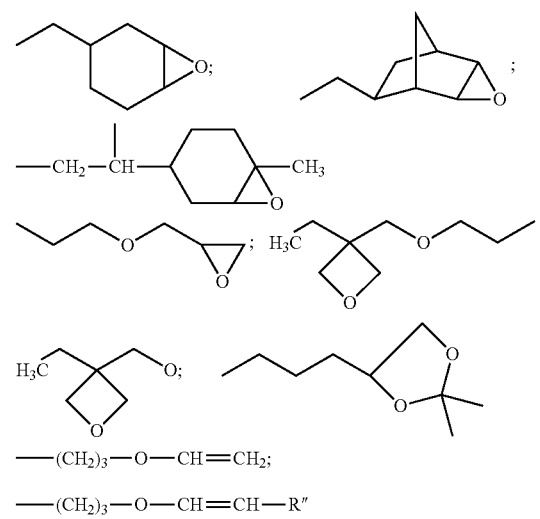

with R″ representing a linear or branched $C_1$-$C_6$ alkyl radical.

According to an advantageous variant of the present invention, the silicone polymer or oligomer consists of at least one silicone having the following average formula:

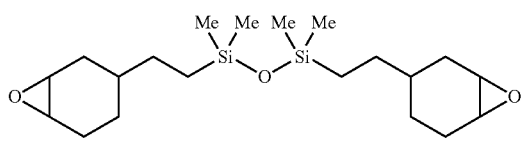
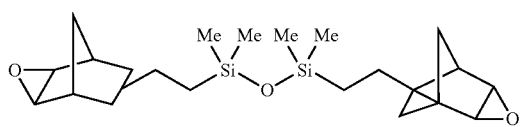
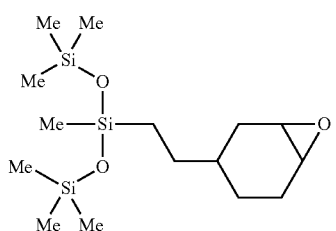
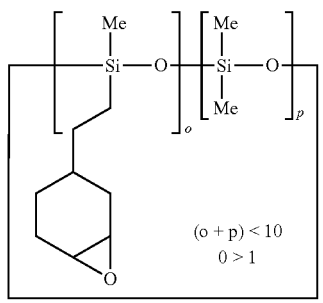
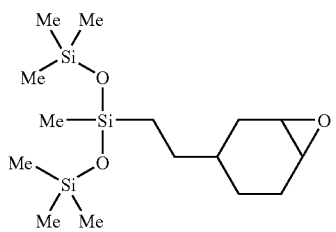
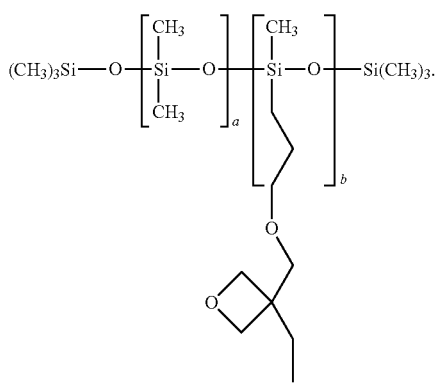
a) 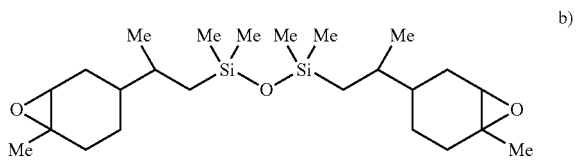 b)
c) 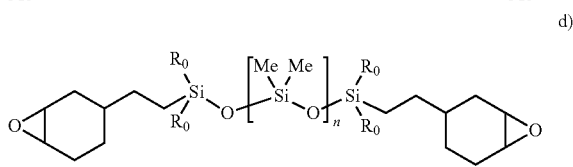 d)
e) 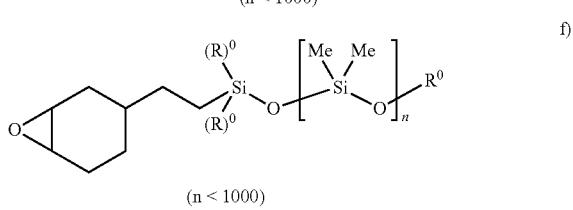 f)
g) 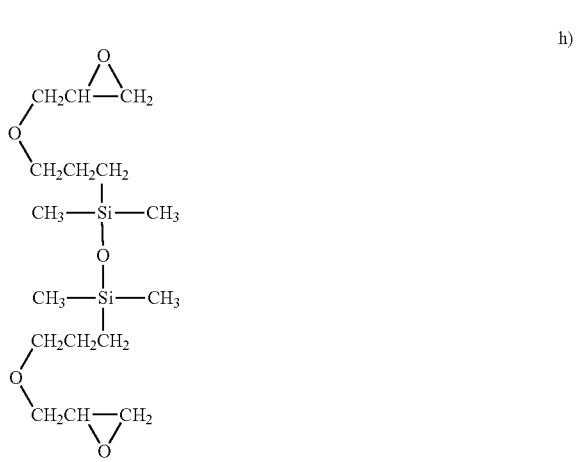 h)
e) 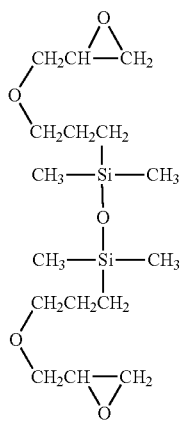
i)

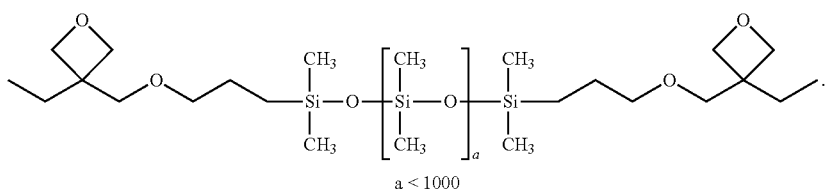
j)

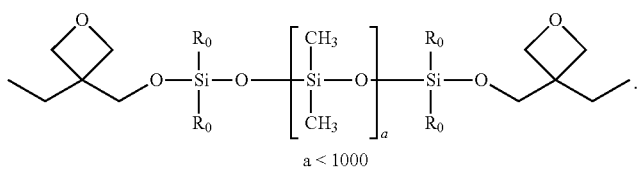
k)

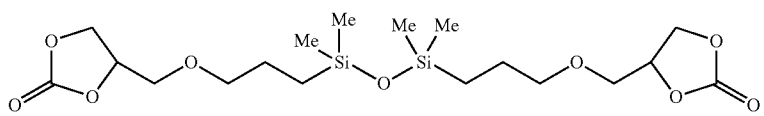
l)

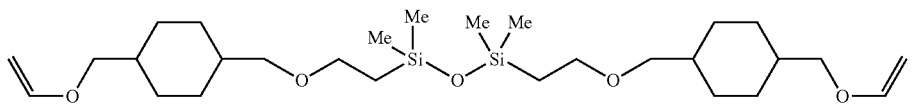
m)

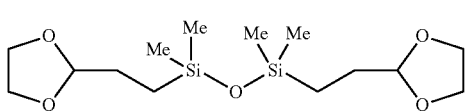
n)

The cationic photoinitiators may be chosen from borates of an organometallic complex (taken on their own or as a mixture with each other) of an element of groups 4 to 10 of the Periodic Table [Chem. & Eng. News, vol. 63, No. 5, 26 of 4 Feb. 1985].

The cationic entity of the borate is selected from the organometallic salts of formula (II):

$$(L^1L^2L^3M)^{+q}$$

in which formula:
M represents a group 4 to 10 metal, in particular iron, manganese, chromium or cobalt,
$L^1$ represents 1 ligand bound to the metal M by π electrons, which ligand is chosen from the ligands $\eta^3$-alkyl, $\eta^5$-cyclopendadienyl and $\eta^7$-cycloheptatrienyl and the $\eta^6$-aromatic compounds chosen from the optionally substituted $\eta^6$-benzene ligands and the compounds having from 2 to 4 condensed rings, each ring being capable of contributing to the valency layer of the metal M by 3 to 8π electrons;
$L^2$ represents a ligand bound to the metal M by π electrons, which ligand is chosen from the ligands $\eta^7$-cycloheptatrienyl and the $\eta^6$-aromatic compounds chosen from the optionally substituted ligands $\eta^6$-benzene and the compounds having from 2 to 4 condensed rings, each ring being capable of contributing to the valency layer of the metal M by 6 or 7π electrons;
$L^3$ represents from 0 to 3 ligands, which are identical or different, linked to the metal M by σ electrons, which ligand(s) is (are) chosen from CO and $NO_2^+$; the total electron charge q of the complex to which $L^1$, $L^2$ and $L^3$ contribute and the ionic charge of the metal M being positive and equal to 1 or 2;
The anionic borate entity has the formula $[BX_aR_b]^-$ (III) in which:

a and b are integers ranging, for a, from 0 to 3 and, for b, from 1 to 4 with a+b=4,
the symbols X represent:
a halogen atom (chlorine, fluorine) with a=0 to 3,
an OH functional group with a=0 to 2,
the symbols R are identical or different and represent:
a phenyl radical substituted with at least one electron-attracting group such as for example $OCF_3$, $CF_3$, $NO_2$, CN, and/or with at least 2 halogen atoms (fluorine most particularly), this being when the cationic entity is an onium of an element of groups 15 to 17,
a phenyl radical substituted with at least one element or one electron-attracting group, in particular a halogen atom (fluorine most particularly), $CF_3$, $OCF_3$, $NO_2$, CN, this being when the cationic entity is an organometallic complex of an element of groups 4 to 10,
an aryl radical containing at least two aromatic nuclei such as for example biphenyl, naphthyl, optionally substituted with at least one electron-attracting group or element, in particular a halogen atom (fluorine most particularly), $OCF_3$, $CF_3$, $NO_2$, CN, regardless of the cationic entity.

In the context of the present invention, the photoinitiators used are selected with a residual absorption of UV light of between 200 and 500 nm, preferably 400 to 500 nm for the preparations of dental prostheses. For dental restoration, a photoinitiator having a residual absorption of UV light above 400 nm will be preferred.

Without being limiting, more details are given below as regards the subclasses of borate of organometallic salts more particularly preferred in the context of the use in accordance with the invention.

According to a first preferred variant of the invention, the entity of the anionic borate entity which are most particularly suitable are the following:

1': $[B(C_6F_5)_4]^-$
2': $[(C_6F_5)_2BF_2]^-$
3': $[B(C_6H_4CF_3)_4]^-$
4': $[B(C_6F_4OCF_3)_4]^-$
5': $[B(C_6H_3(CF_3)_2)_4]^-$
6': $[B(C_6H_3F_2)_4]^-$
7': $[C_6F_5BF_3]^-$

According to a second preferred variant, the organometallic salts (4) which can be used are described in the documents U.S. Pat. No. 4,973,722, U.S. Pat. No. 4,992,572, EP-A-203 829, EP-A-323 584 and EP-A-354 181. The organometallic salts most readily selected according to the invention are in particular:

($\eta^5$-cyclopentadienyl)($\eta^6$-toluene) $Fe^+$,
($\eta^5$-cyclopentadienyl)($\eta^6$-methyl-1-naphthalene) $Fe^+$,
($\eta^5$-cyclopentadienyl)($\eta^6$-cumene) $Fe^+$,
bis($\eta^6$-mesitylene) $Fe^+$,
bis($\eta^6$-benzene) $Cr^+$.

In agreement with these three preferred variants, the following products may be mentioned by way of examples of photoinitiators of the onium borate type:

($\eta^5$-cyclopentadienyl)($\eta^6$-toluene) $Fe^+$, $[B(C_6F_5)_4]^-$
($\eta^5$-cyclopentadienyl)($\eta^6$-methyl-1-naphthalene) $Fe^+$, $[B(C_6F_5)_4]^-$
($\eta^5$-cyclopentadienyl) ($\eta^6$-cumene) $Fe^+$, $[B(C_6F_5)_4]^-$ As another literary reference for defining the borates of organometallic salts (4), there may be mentioned the entire content of patent applications EP 0 562 897 and 0 562 922. This content is integrally incorporated by reference into the present disclosure.

In addition to the principal components of the dental composition, it may comprise at least one aromatic hydrocarbon photosensitizer with one or more aromatic nuclei which are substituted or not, having a residual light absorption of between 200 and 500 nm.

This photosensitizer may be highly varied. It may correspond in particular to one of the following formulae (IV) to (XXII):

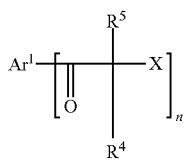

formula (IV)
in which:
when n=1, $Ar^1$ represents an aryl radical containing from 6 to 18 carbon atoms, a tetrahydronaphthyl, thienyl, pyridyl or furyl radical or a phenyl radical carrying one or more substituents chosen from the group consisting of F, Cl, Br, CN, OH, linear or branched $C_1$-$C_{12}$ alkyls, —$CF^3$, —$OR^6$, —OPhenyl, —$SR^6$, —SPhenyl, —$SO_2$Phenyl, —$COOR_1$—O—($CH_2$—CH=$CH_2$), —O($CH_2H_4$—O)$_m$—H, —O($C_3H_6O$)$_m$—H, m being between 1 and 100,
when n=2, $Ar^1$ represents a $C_6$-$C_{12}$ arylene radical or a phenylene-T-phenylene radical where T represents —O—, —S—, —$SO_2$— or —$CH_2$—,
X represents a group —$OR^7$ or —$OSiR^8(R^9)_2$ or forms, with $R^4$, a group —O—CH($R^{10}$)—,
$R_4$ represents a linear or branched $C_1$-$C_8$ alkyl radical which is unsubstituted or which carries an —OH, —$OR^6$, $C_2$-$C_8$ acyloxy, —$COOR^6$, —$CF^3$ or —CN group, a $C_3$ or $C_4$ alkenyl radical, a $C_6$ to $C_{18}$ aryl radical, a $C_7$ to $C_9$ phenylalkyl radical,
$R^5$ has one of the meanings given for $R^4$ or represents a radical —$CH_2CH_2R^{11}$, or alternatively forms with $R^4$ a $C_2$-$C_8$ alkylene radical or a $C_3$-$C_9$ oxa-alkylene or aza-alkylene radical,
$R^6$ represents a lower alkyl radical containing from 1 to 12 carbon atoms,
$R^7$ represents a hydrogen atom, a $C_1$-$C_{12}$ alkyl radical, a $C_2$-$C_6$ alkyl radical carrying an —OH, —$OR^6$ or —CN group, a $C_3$-$C_6$ alkenyl radical, a cyclohexyl or benzyl radical, a phenyl radical optionally substituted with a chlorine atom or a linear or branched $C_1$-$C_{12}$ alkyl radical, or a 2-tetrahydropyranyl radical,
$R^8$ and $R^9$ are identical or different and each represent a $C_1$-$C_4$ alkyl radical or a phenyl radical,
$R^{10}$ represents a hydrogen atom, a $C_1$-$C_8$ alkyl radical or a phenyl radical,
$R^{11}$ represents a radical —$CONH_2$, —$CONHR^6$, —$CON(R^6)_2$, —P(O) $(OR^6)_2$ or 2-pyridyl;

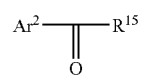

formula (V)
in which:
$Ar^2$ has the same meaning as $Ar^1$ of formula (IV) in the case where n=1,
$R^{15}$ represents a radical chosen from the group consisting of a radical $Ar^2$, a radical —(C=O)-$Ar^2$, a linear or branched $C_1$-$C_{12}$ alkyl radical, a $C_6$-$C_{12}$ cycloalkyl radical, and a cycloalkyl radical forming a $C_6$-$C_{12}$ ring with the carbon of the ketone or a carbon of the radical $Ar^2$, it being possible for these radicals to be substituted with one or more substituents chosen from the group consisting of —F, —Cl, —Br, —CN, —OH, —$CF_3$, —$OR^6$, —$SR^6$, —$COOR^6$, the linear or branched $C_1$-$C_{12}$ alkyl radicals optionally carrying an —OH, —$OR^6$ and/or —CN group, and the linear or branched $C_1$-$C_8$ alkenyl radicals;

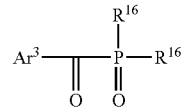

formula (VI)
in which:
$Ar^3$ has the same meaning as $Ar^1$ of formula (IV) in the case where n=1,
$R^{16}$, identical or different, represents a radical chosen from the group consisting of a radical $Ar^3$, a radical —(C=O)—$Ar^3$, a linear or branched $C_1$-$C_{12}$ alkyl radical, a $C_6$-$C_{12}$ cycloalkyl radical, it being possible for these radicals to be substituted with one or more substituents chosen from the group consisting of —F, —Cl, —Br, —CN, —OH, —$CF_3$, —$OR^6$, —$SR^6$, —$COOR^6$, the linear or branched $C_1$-$C_{12}$ alkyl radicals optionally carrying an —OH, —$OR^6$ and/or —CN group, and the linear or branched $C_1$-$C_8$ alkenyl radicals;

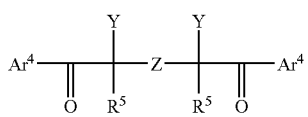

formula (VII)

in which:

$R^5$, which are identical or different, have the same meanings as in formula (III), Y, which are identical or different, represent X and/or $R^4$, Z represents:

a direct bond, a $C_1$-$C_6$ divalent alkylene radical, or a phenylene, diphenylene or phenylene-T-phenylene radical, or alternatively forms, with the two substituents $R^5$ and the two carbon atoms carrying these substituents, a cyclopentane or cyclohexane nucleus, a divalent group —O—$R^{12}$—O—, —O—$SiR^8R^9$—O—$SiR^8R^9$—O—, or —O—$SiR^8R^9$—O—, $R^{12}$ represents a $C_2$-$C_8$ alkylene, $C_4$-$C_6$ alkenylene or xylylene radical, and $Ar^4$ has the same meaning as $Ar^1$ of formula (IV) in the case where n=1.

family of thioxanthones of formula (VIII):

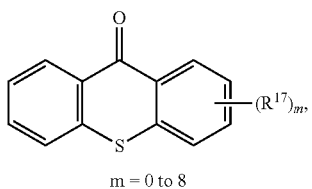

m = 0 to 8

$R^{17}$, identical or different substituent(s) on the aromatic nucleus (nuclei), represent a linear or branched C1-C12 alkyl radical, a C6-C12 cycloalkyl radical, a radical $Ar^1$, a halogen atom, an —OH, —CN, —$NO_2$, —$COOR^6$, —CHO, Ophenyl, —$CF_3$, —$SR^6$, —Sphenyl, —$SO_2$phenyl, Oalkenyl, or —$SiR^6_3$ group.

family of xanthenes of formula (IX):

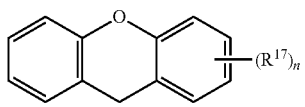

n = 0 to 8 family of xanthones of formula (X):

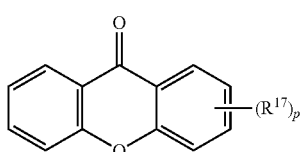

p = 0 to 8 family of the naphthalene of formula (XI):

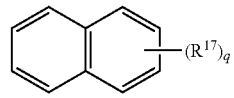

q = 0 to 8 family of the anthracene of formula (XII):

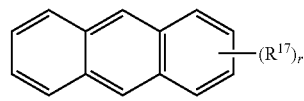

r = 0 to 10 family of the phenanthrene of formula (XIII):

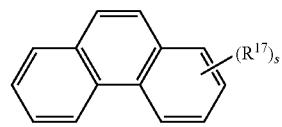

s = 0 to 10 family of the pyrene of formula (XIV):

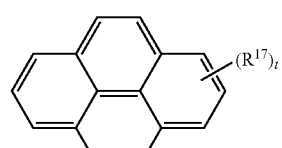

t = 0 to 10 family of the fluorene of formula (XV):

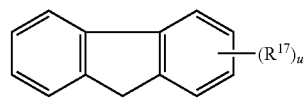

u = 0 to 9 family of the fluoranthene of formula (XVI):

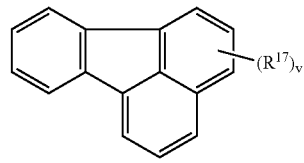

v = 0 to 10 family of the chrysene of formula (XVII):

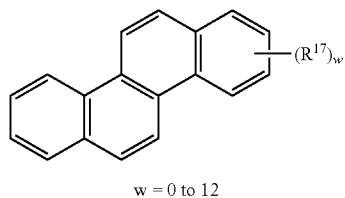

w = 0 to 12 family of the fluorene of formula (XVIII):

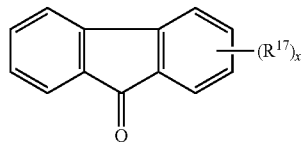

with x=0 to 8, for example 2,7-dinitro-9-fluorenone, family of the chromone of formula (XIX):

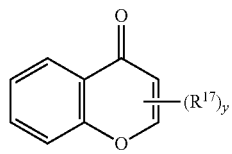

with y = 0 to 6 family of the eosin of formula (XX):

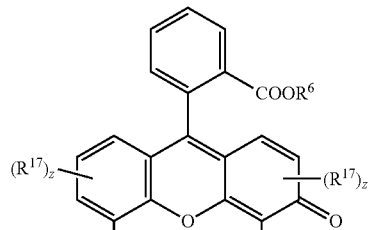

with z = 0 to 5

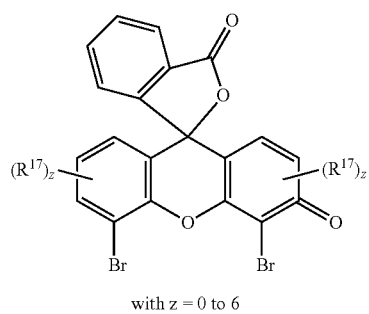

with z = 0 to 6 family of the erythrosin of formula (XXI):

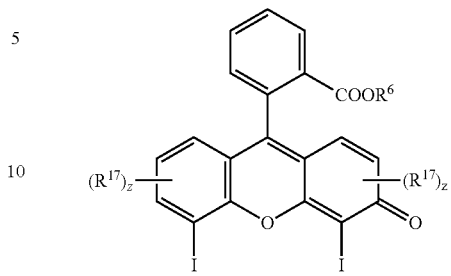

with z = 0 to 5

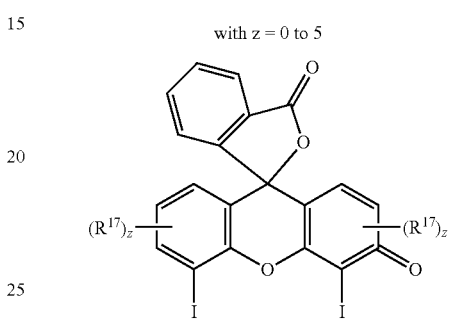

with z = 0 to 6 family of the biscoumarins of formula (XXII):

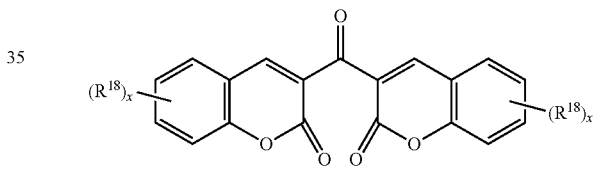

$R^{18}$, identical or different, has the same meaning as $R^{17}$ or represents a group —$NR^6_2$, for example 3,3'-carbonyl-bis(7-diethylaminocoumarin) and 3,3'-carbonyl-bis(7-methoxycoumarin).

Other sensitizers can be used. In particular, the photosensitizers described in the documents U.S. Pat. Nos. 4,939,069; 4,278,751; 4,147,552 may be used.

In the context of the present invention, as in the case of photoinitiators, the photosensitizers have a residual absorption of UV light between 200 and 500 nm, preferably 400 to 500 nm for the preparations of dental prostheses. For dental restoration, a photosensitizer having a residual absorption of UV light above 400 nm will be preferred.

According to a preferred variant, the photosensitizers will be chosen from those of the families (IV), (VII) and (VIII). By way of examples, the following photosensitizers will be mentioned:

4,4'-dimethoxybenzoin; phenanthrenequinone 2-ethylan-thraquinone; 2-methylanthraquinone; 1,8-dihydroxyan-thraquinone; Dibenzoylperoxide; 2,2-dimethoxy-2-phe-nylacetophenone; benzoin; 2-hydroxy-2-methylpropiophenone; benzaldehyde; 4-(2-hydroxyethoxy)phenyl-(2-hydroxy-2-methylpropyl)-ketone;

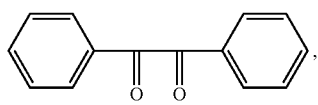

benzoylacetone;

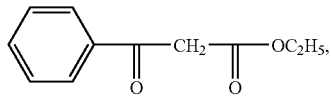

2-isopropylthioxanthone; 1-chloro-4-propoxy-thioxanthone; 4-isopropylthioxanthone; 2-4-diethylthioxanthone and the mixture thereof.

Various types of fillers can be used for preparing the compositions according to the invention. The fillers are chosen according to the final use of the dental composition: these affect important properties such as appearance, penetration of UV radiation, as well as the mechanical and physical properties of the material obtained after crosslinking and/or polymerization of the dental composition.

As reinforcing filler, there may be used treated or untreated pyrogenic silica fillers, amorphous silica fillers, quartz, glass or nonglassy fillers based on oxides of zirconium, barium, calcium, fluorine, aluminum, titanium, zinc, borosilicates, aluminosilicates, talc, spherosil, yterbium trifluoride, fillers based on polymers in ground powder form, such as inert or functionalized methyl polymethacrylates, polyepoxides or polycarbonates.

By way of example, there may be mentioned:

inert fillers based on methyl polymethacrylate LUXAS-ELF from the company UGL, which can be used in the dental field and which are pigmented in pink, hexamethyldisilazane-treated fumed silica fillers having a specific surface area of 200 m²/g, untreated fumed silica fillers (Aerosil product AE200 marketed by DEGUSSA).

According to an advantageous variant of the invention, the fillers and in particular the silica fillers are treated before use at 120° C. with a quantity of less than 10% w/w of silicone comprising at least one unit of formula (XXIII):

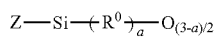

such that Z' has the same definition as Z
a=0, 1, 2 or 3
with at least one silicon atom.

There may be mentioned by way of example the polymer described below with Z=epoxide and Z=trialkoxysilyl

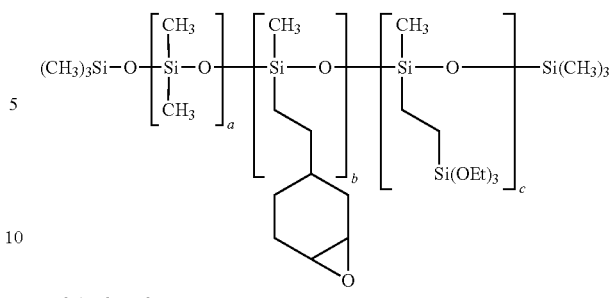

a = 9; b = 2; c = 2

In this case for the treatment of silicone-containing filler(s), in particular silica, with this type of polymer, the material obtained after crosslinking has a mechanical strength, a modulus of elasticity and a resistance to compression which are markedly improved.

In addition to the reinforcing fillers, pigments may be used to color the dental composition according to the invention envisaged and the ethnic groups.

For example, red pigments are used in the presence of microfibers for the dental compositions used for the preparation of dental prostheses in order to simulate the blood vessels.

Pigments based on metal oxides (iron and/or titanium and/or aluminum and/or zirconium oxides, and the like) are also used for the dental compositions used for the preparation of restoration material, in order to obtain a crosslinked material having an ivory color.

Other additives may be incorporated into the dental compositions according to the invention. For example, biocides, stabilizers, flavoring agents, plasticizers and adherence promoters.

Among the additives which may be envisaged, there will be advantageously used crosslinkable and/or polymerizable coreagents of the organic type. These coreagents are liquid at room temperature or are hot-meltable at a temperature of less than 100° C., and each coreagent comprises at least two reactive functional groups such as oxetane-alkoxy, oxetane-hydroxyl, oxetane-alkoxysilyl, carboxyl-oxetane, oxetane-oxetane, alkenyl ether-hydroxyl, alkenyl ether-alkoxysilyl, epoxy-alkoxy, epoxy-alkoxysilyls, dioxolane-dioxolane-alcohol, and the like.

The dental compositions according to the invention may be used for numerous dental applications, and in particular in the field of dental prostheses, in the field of dental restoration and in the field of temporary teeth.

The dental composition according to the invention is preferably provided in the form of a single product containing the various components ("monocomponent") which facilitates its use, in particular in the field of dental prostheses. Optionally, the stability of this "monocomponent" product may be provided for by organic derivatives with amine functional groups according to the teaching of the document WO 98/07798.

In the "monocomponent" form, the product may for example be deposited with the aid of a syringe directly on the plaster model or in a core. Next, it is polymerized (polymerization by possible successive layers) with the aid of a UV lamp (visible light spectrum 200-500 nm). In general, the production of an esthetic and lasting dental prosthesis is carried out in 10 to 15 min.

It should be noted that the products obtained from the dental composition according to the invention are nonporous.

Thus, after an optional polishing with the aid of a felt brush, for example, the surface of the dental prostheses obtained is smooth and bright and therefore does not require the use of varnish.

The applications in the field of dental prostheses are essentially those of the joined prosthesis, which can be divided into two types:
- full prosthesis in the case of a patient with absolutely no teeth
- partial prosthesis due to the absence of several teeth, resulting either in a provisional prosthesis, or a skeleton brace.

In the field of dental restoration, the dental composition according to the invention may be used as material for filling the anterior and posterior teeth in different colors (for example "VITA" colors), which is rapid and easy to use.

The dental composition being nontoxic and polymerizable in thick layers, it is not essential to polymerize the material in successive layers. In general, a single injection of the dental composition is sufficient.

The preparations for dental prostheses and for restoration materials are carried out according to techniques which are customary in the art.

In the case of application of the dental composition as a tooth, either the tooth may be pretreated with a bonding primer or the dental composition may be prepared as a mixture with a bonding primer before its use. However, it is not essential to use a bonding primer in order to use the dental composition according to the invention.

The following examples and tests are given by way of illustration. They make it possible in particular to understand more clearly the invention and to highlight some of its advantages and to illustrate a few of its variant embodiments.

EXAMPLES AND TESTS

The product used in the compositions of the examples are the following:

product (A):

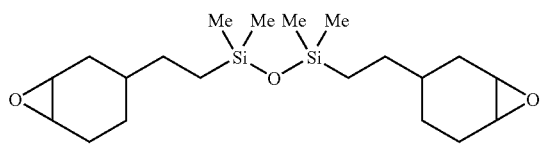

Product (B): this product is a mixture of siloxanes, whose viscosity is 23.5 mPa·s and in which the proportions by weight and formulae $B_1$, $B_2$ and $B_3$ are given below:

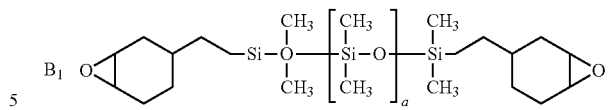

with 89% of $B_1$ where a=0, 9% of $B_1$ where a=1; 0.2% of $B_1$ where a=2;

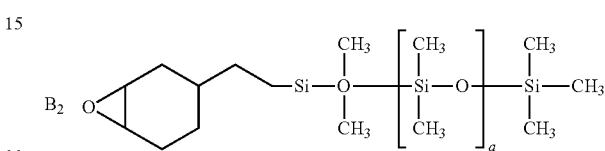

with 0.3% of $B_2$ where a=0;

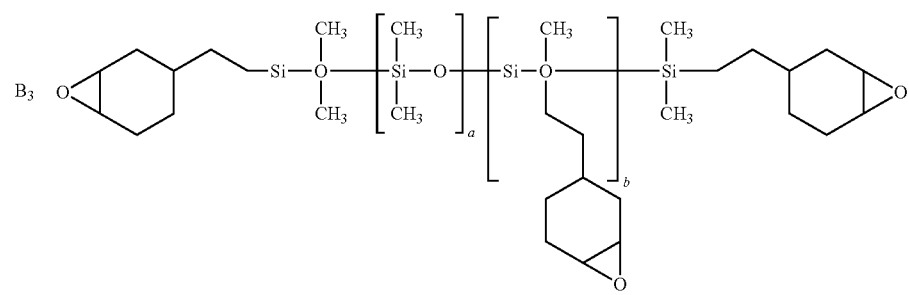

and with 1.5% of $B_3$ where a=0 and b=1.

product (P1): -($\eta^5$-cyclopentadienyl) ($\eta^6$-toluene) $Fe^+$, $[B(C_6F_5)_4]^-$.

Example 1

Composition for Dental Prosthesis

The following are mixed using a three-blade stirrer:
- 100 parts of siloxane (A) stabilized with 50 ppm of Tinuvin 765;
- 1 part of photoinitiator (P1) at 75% in ethyl acetate;
- 150 parts of a pink-pigmented, polymethyl methacrylate-based inert filler (product LUXASELF from UGL dentaire).

The composition obtained is stable in the absence of light for several months at room temperature. This composition can be worked manually and for several hours in the presence of daylight.

A test piece 2.8±0.3 mm thick is prepared in a glass dish 64 mm long (model), 10 mm wide (model) and open at the top by pouring the prepared composition ("monocomponent") into the dish.

The composition is dried by passing the dish for 1 to 2 seconds (3 m/min) under a UV lamp of 200 W/cm power corresponding to the excitation of a mixture of mercury and gallium and emitting in the UV-visible range above 400 nm.

The product obtained is unmolded by breaking the glass.

The SHORE D hardness of the two polymerized compositions is determined on each side of the item made immediately after crosslinking.

| Example 1 | Immediate measurement | Measurement after 10 hours |
|---|---|---|
| Irradiated surface: | 50 | 80 |
| Bottom surface | 40 | 80 |

The Shore D hardness continues to change substantially over a few hours.

The volume shrinkage is very low and excellent size stability is obtained.

The loss of mass is less than 1%.

The product may be used with or without bonding primer in the presence of artificial teeth or of natural teeth.

More generally, the properties of the material obtained are in agreement with the DIN/ISO 1567 standard.

Example 2

Dental Composition

This composition is formulated with:
95 parts of silicone (B),
0.5 part of photoinitiator (P1) at 10% in siloxane (B),
5 parts of the oxetane 3-ethyl-3-(hydroxymethyl)oxetane,
and 120 parts of precipitated silica (ground quartz).

The crosslinking-polymerization operation is carried out using a lamp emitting a light spot emitted through a curved light tip 8 mm in diameter. The source is an Optibulb 80 W lamp (DEMETRON Optilux 500) for wavelengths of between 400 and 520 nm.

The dental composition is applied in a tooth. A thickness of 5 mm is crosslinked in less than 30 seconds.

The stiffness values found are greater than 60 Mpa according to the ISO 1567 standard.

Example 3

Composition for Dental Prosthesis or Dental Restoration Material

The following are mixed using a three-blade stirrer:
100 parts of silicone (B),
0.5 part of photoinitiator (P1) at 10% in solution in silicone (B),
and 120 parts of precipitated silica (ground quartz).

A mixture is obtained which is opaque, gray in color, nonflowing and capable of being handled.

The crosslinking operation is carried out in a manner identical to that of Example 2. A composition 5 mm thick is crosslinked in less than 30 seconds. The color of the material after crosslinking is similar to ivory color.

The composition, in this case, is suitable in particular for dental prostheses, in particular the stiffness is greater than 60 Mpa according to the ISO 1567 standard.

The invention claimed is:

1. A dental composition comprising:
   (1) crosslinkable or polymerizable silicone monomers which are a mixture of compounds of the formula:

(i) wherein a=0, 1 or 2;

(ii) wherein a=0; and (iii) wherein a=0 and b=1;
   said crosslinkable or polymerizable monomers being the only crosslinkable or polymerizable monomers in the composition,
   (2) at least one dental filler present in a proportion of at least 10% by weight relative to the total weight of the composition, and
   (3) an effective quantity of at least one organometallic complex borate photoinitiator having a residual light absorption of between 200 and 500 nm, the photoinitiator having a cationic and a borate anionic entity, said cationic entity being of formula (II):

$$(L^1 L^2 L^3 M)^{+q},$$

wherein:
   M represents a group 4 to 10 metal,
   $L^1$ represents 1 ligand bound to the metal M by π by electrons, said ligand being $\eta^3$-alkyl, $\eta^5$-cyclopendadienyl, $\eta^7$-cycloheptratrienyl and optionally substituted $\eta^6$-benzene having from 2 to 4 condensed rings, each ring being capable of contributing to the valency layer of the metal M by 3 to 8 π electrons;
   $L^2$ represents a ligand bound to the metal M by π electrons, said ligand being $n^7$-cycloheptratrienyl or $n^6$-benzene and the compounds having from 2 to 4 condensed rings, each ring being capable of contributing to the valency layer of the metal M by 6 or 7 π electrons;
   $L^3$ represents from 0 to 3 ligands, which are identical or different, linked to the metal M by σ electrons, said ligand(s) being CO or $NO_2^+$; the total electron charge q of the complex to which $L^1$, $L^2$ and $L^3$ contribute and the ionic charge of the metal M being positive and equal to 1 or 2; and said anionic borate being of formula (III):

$[BX_aR_b]^-$ wherein:
a and b are integers ranging, for a, from 0 to 3 and, for b, from 1 to 4 with a+b=4, the symbols X represent:
a halogen atom with a=0 to 3, or
an OH functional group with a=0 to 2,
the symbols R are identical or different and represent:
a phenyl radical substituted with at least one electron-attracting group or with at least 2 halogen atoms, this being when the cationic entity is an onium of an element of groups 15 to 17,
a phenyl radical substituted with at least one element or one electron-attracting group, this being when the cationic entity is an organometallic complex of an element of groups 4 to 10, or
an aryl radical containing at least two aromatic nuclei, optionally substituted with at least one electron-attracting group or element, regardless of the cationic entity.

2. The dental composition as claimed in claim 1, wherein the compound of the formula (i) is present in said mixture in an amount of 89% by weight where a=0, 9% by weight where a=1 and 0.2% by weight where a=2; the compound of formula (ii) is present in said mixture in an amount of 0.3% by weight; and the compound of formula (iii) is present in said mixture in an amount of 1.5% by weight.

3. The dental composition as claimed in claim 2, wherein the photoinitiator is:

$(\eta^5\text{-cyclopentadienyl})(\eta^6\text{-toluene}) Fe^+, [B(C_6F_5)_4]^-$.

4. The dental composition as claimed in claim 1, wherein the photoinitiator is:

$(\eta\text{-cyclopentadienyl})(\eta^6\text{-toluene}) Fe^+, [B(C_6F_5)_4]^-$.

5. The composition as claimed in claim 1, wherein the photoinitiator is:
$(\eta^5\text{-cyclopentadienyl})(\eta^6\text{-toluene}) Fe^+, [B(C_6F_5)_4]^-$
$(\eta^5\text{-cyclopentadienyl})(\eta^6\text{-methyl-1-naphthalene}) Fe^+, [B(C_6F_5)_4]^-$ or
$(\eta^5\text{-cyclopentadienyl})(\eta^6\text{-cumene}) Fe^+, [B(C_6F_5)_4]^-$.

6. The composition as claimed in claim 1, wherein the dental composition comprises at least one aromatic hydrocarbon photosensitizer with one or more optionally substituted aromatic nuclei, having a residual light absorption of between 200 and 500 nm.

7. The dental composition as claimed in claim 1, provided in the form of a monocomponent composition.

8. The dental composition as claimed in claim 1, wherein said composition has a stiffness value of greater than 60 Mpa according to ISO 1567 standard upon cross-linking/polymerization.

9. The dental composition as claimed in claim 1, wherein said composition has a Shore D hardness of at least 40 measured immediately upon cross-linking/polymerization.

* * * * *

UNITED STATES PATENT AND TRADEMARK OFFICE
CERTIFICATE OF CORRECTION

| | | |
|---|---|---|
| PATENT NO. | : 8,262,391 B2 | Page 1 of 1 |
| APPLICATION NO. | : 11/370817 | |
| DATED | : September 11, 2012 | |
| INVENTOR(S) | : Jean-Marc Frances | |

It is certified that error appears in the above-identified patent and that said Letters Patent is hereby corrected as shown below:

On Title page, please add to Section (65) Prior Publication Data:
WO 00/19966 A1 April 13, 2000;

On Title page, please correct Section (63) Related U.S. Application Data to read:
Continuation of application No. 09/806,648, filed on Jun. 2, 2003, now abandoned, filed as 371 of International application No. PCT/FR99/02344, filed on October 1, 1999.

Signed and Sealed this
Nineteenth Day of February, 2013

Teresa Stanek Rea
*Acting Director of the United States Patent and Trademark Office*